United States Patent [19]

Sunna

[11] 4,343,199
[45] Aug. 10, 1982

[54] SAMPLING DEVICE

[75] Inventor: G. Sigvard Sunna, Skellefteå, Sweden

[73] Assignee: Boliden Aktiebolag, Stockholm, Sweden

[21] Appl. No.: 200,493

[22] PCT Filed: Nov. 30, 1979

[86] PCT No.: PCT/SE79/00242
§ 371 Date: Aug. 4, 1980
§ 102(e) Date: Jul. 1, 1980

[87] PCT Pub. No.: WO80/01205
PCT Pub. Date: Jun. 12, 1980

[30] Foreign Application Priority Data

Dec. 4, 1978 [SE] Sweden .............................. 7812470

[51] Int. Cl.³ .............................................. G01N 1/20
[52] U.S. Cl. ................................ 73/863.43; 73/863.51
[58] Field of Search ............ 73/863.41, 863.43, 863.51

[56] References Cited

U.S. PATENT DOCUMENTS 2,670,629  3/1954  Belden ............................. 73/863.43
3,999,438  12/1976  Sundvist .......................... 73/863.51

Primary Examiner—S. Clement Swisher

Attorney, Agent, or Firm—Stevens, Davis, Miller & Mosher

[57] ABSTRACT

A device for taking from a flowing suspension a sample-flow representative of said suspension comprises a first chamber (18) arranged to receive the flowing suspension, said first chamber communicating via a weir (23) with the upper part of a second chamber (22) having first and second openings (25, 26) arranged at the bottom thereof for removing the sample-flow and the remaining part of said suspension respectively. The openings, (25, 26) are separated from each other by partition walls (27) which extend transversely of the weir over the whole length of the second chamber and communicate with a respective outlet (15, 20; 21). The openings (26) for receiving the said remaining part of the suspension communicate with the associated outlet (21) via a substantially U-shaped passage and a second weir (29) which is located substantially on the same level as the weir (23) of the first chamber. In order to prevent blockage of the U-shaped passage while maintaining requisite precision of the device, at least one of said partition walls (27) exhibits means for maintaining communication between said U-shaped passage and the sample-flow outlet (15, 20) in a region located beneath the uppermost level (33) of the connection (30) between the two legs of the U-shaped passage.

5 Claims, 2 Drawing Figures

U.S. Patent     Aug. 10, 1982     4,343,199
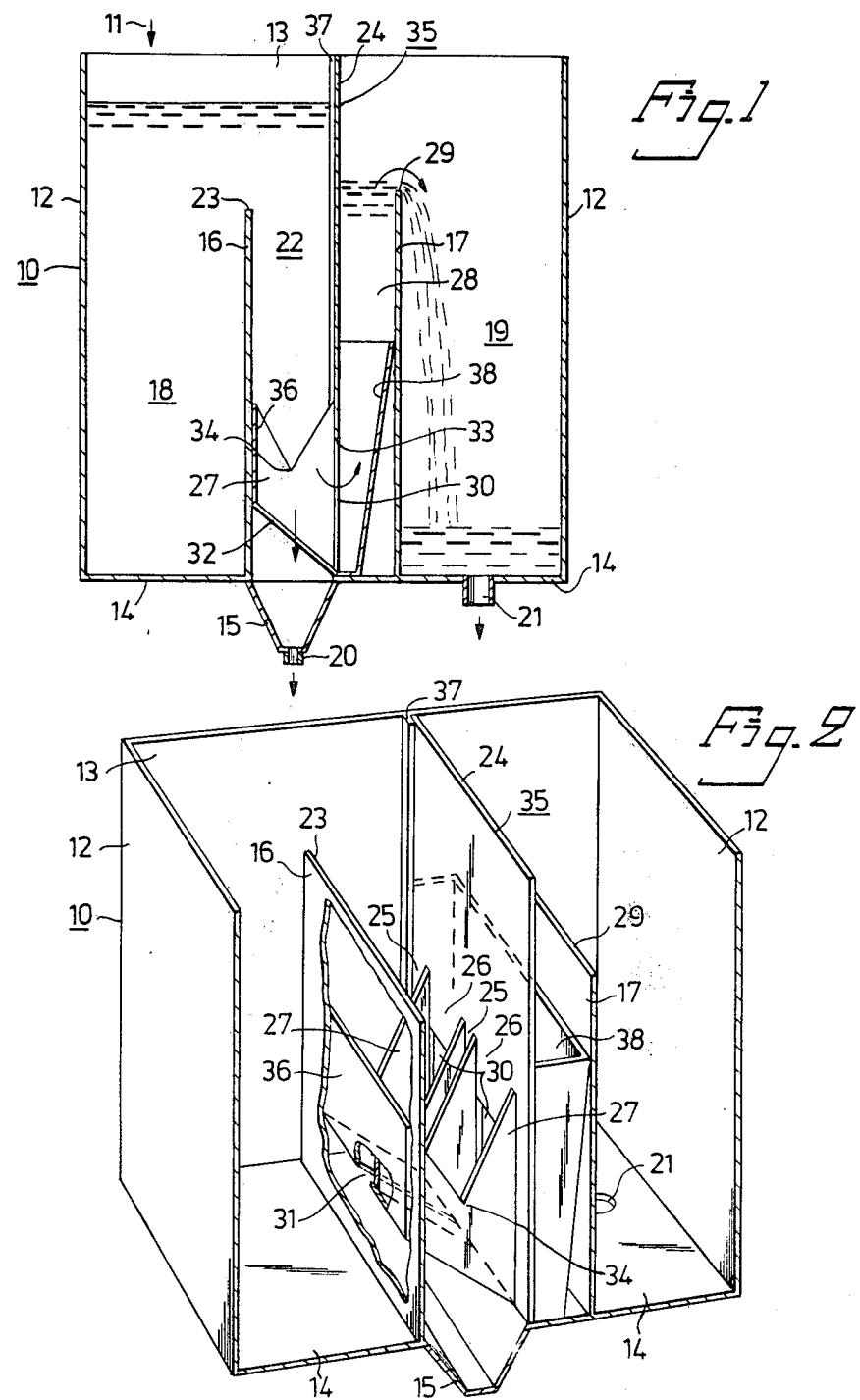

SAMPLING DEVICE

The present invention relates to a device for taking from a flowing suspension a sample-flow which is of substantially constant flow rate and which is representative of the composition of said suspension, said device being of the kind which comprises a first chamber arranged to receive the flowing suspension and which communicates via a weir, with the upper part of a second chamber having first and second openings arranged at the bottom thereof for the removal of the sample-flow and the remaining part of the suspension respectively, said openings being separated from one another by partition walls which extend transversely of said weir over the whole length of the second chamber; and in which the second openings communicate with an outlet via a substantially U-shaped passage and a second weir whose lip is located substantially on the same level as the lip of the weir of the first chamber, while the first openings communicate with a second outlet which is so adapted that with normal flow of the suspension entering the first chamber the flow rate of said suspension into the first openings is substantially equal to the flow rate of said suspension into the second openings.

A device of this kind is known, for example, from U.S. Pat. No. 3,999,438. The accuracy of this known sampling device is extremely high when said device is used under favourable conditions, namely with large suspension flows which fluctuate only slightly. One disadvantage with the known device, however, is that when using said device to sample suspension flows which vary greatly, and in particular when sampling such flows which periodically halt completely, there is required a relatively large opening in the lower part of the U-shaped passage for removing sediment therefrom. In turn, the presence of this opening in the lower part of the U-shaped passage requires relatively large flows of suspension during a sampling operation, in order to ensure the requisite flow of suspension over the said second weir in order for a correct sampling result to be obtained.

The object of the present invention is to provide a sampling device of the kind hereinbefore described whose construction enables the aforementioned disadvantage to be at least substantially eliminated.

To this end it is proposed in accordance with the invention that at least one of said partition walls exhibits means for maintaining communication between the U-shaped passage and said second outlet in a region located beneath the uppermost level of the connection between the two legs of the U-shaped passage. By means of this arrangement, complete blockage of the U-shaped passage is prevented when the flow of suspension passing therethrough is slight or when said flow ceases completely. When the flow of suspension is subsequently increased, particles which have settled in the bottom portion of the U-shaped passage will be caused to swirl and accompany substantially only that part of the suspension which departs through the U-shaped passage and over said second weir, whereby the connecting region between the two legs of U-shaped passage will be completely cleansed and reopened. Thus, the sampling device is self-cleaning.

The means for maintaining communication between the U-shaped passage and the second outlet may, for example, comprise holes or slots in one or more of the partition walls, although a more favourable arrangement from the aspect of accuracy is obtained by causing the upper side of at least one of said partition walls to slope downwardly from the opposite ends of the partition wall, from locations above the uppermost level of the connection between the two legs of the U-shaped passage, to a position located at a distance beneath said uppermost level and at a distance from both ends of the partition wall. In practice it has been found most suitable to provide said upper side with a substantially symmetrical V-shape, the most favourable result with respect to correspondence of the sample-flow with the composition of the supplied suspension and the self-cleaning effect of the device being normally obtained when the upper side parts forming the V-configuration enclose an angle of about 50°–135°.

A particularly suitable embodiment of the sampling device according to the invention from the aspect of manufacture and maintenance comprises a substantially right-angled parallelepipedic vessel, at least one of said weirs being formed by the upper edge of a fixed wall extending parallel with and located at a distance from the end walls of said vessel, and in which said U-shaped passage and said first and second openings are formed in an insert which can be localized in said vessel in a predetermined position adjacent the cross wall, the bottom of the vessel beneath the insert, when said insert is mounted in said position, having the form of a trough for collecting and conducting away the sample-flow arriving from said first openings. This arrangement permits the sampling device to be optimally adapted to different suspensions and/or different normal flows, by changing one kind of insert for another.

The invention will now be described in more detail with reference to the accompanying drawing, in which FIG. 1 is a longitudinal sectional view of a preferred embodiment of the sampling device according to the invention; and FIG. 2 is a perspective view of the device shown in FIG. 1, portions being cut away to show the construction of the device more clearly.

The illustrated device for removing from a flowing suspension, e.g. a flotation pulp containing air bubbles, a sample-flow which is of constant flow rate and which is representative of the composition of said suspension with the exception of its air bubble content, comprises a right-angled parallelepipedic vessel generally shown at 10 having a suspension inlet shown by the arrow 11. The vessel 10 has end walls 12, said end walls 12 connecting side walls 13, of which only one has been shown in the drawing, and a bottom 14 whose central part is lowered to form a funnel- or trough-like part 15. The vessel is divided into an inlet chamber 18 and an outlet chamber 19 by means of transversal intermediate walls 16, 17 which terminate below the upper edge of the vessel 10, said chambers being separated by an intermediate space located between the walls 16, 17. The references 20 and 21 identify outlets arranged in the respective bottoms of the part 15 and the chamber 19, for the sample-flow and the remaining flow respectively. The chamber 18 receives the incoming suspension through the inlet and retards said suspension. The suspension departs from the chamber 18 to a further chamber 22 via a weir 23 formed by the upper edge of the wall 16.

The chamber 22 is defined by the side walls 13 of the vessel, the intermediate wall 16 and a further transversal intermediate wall 24 located between said intermediate wall 16 and the wall 17, said intermediate wall 24 extending from the bottom 14 to the upper edge of the vessel 10. The chamber 22 is provided at the bottom thereof with first and second openings 25 and 26, which are defined by partition walls 27 extending between the walls 16 and 24 parallel with the side walls 13, and by portions of the side walls 13, the sample-flow and the remaining part of the suspension departing through respective ones of said openings. As with the inlet chamber 18, the chamber 22 is of considerable dimension so that non-turbulent smooth flow conditions are obtained for the suspension, which also flows quietly over the weir 23. In this way air bubbles present in the incoming suspension are able to rise to the surface and depart, so that the suspension reaching the openings 25 and 26 is substantially free from air bubbles. When seen in plan view, the openings 25, 26 have the shape of slots extending transversely of the weir 23 and form a respective mouth of vertical conduits. The openings 25, which receive the sample-flow, and the conduits associated with said openings are narrower than the openings 26 and the conduits associated therewith, receiving the remainder of the suspension, such that the sample-flow is smaller than the flow through the openings 26.

The openings 26 communicate with the outlet 21 through a device arranged to exert a counterpressure on the suspension passing through said openings 26. More specifically, the conduits which conduct the said remaining part of the suspension and which are associated with the openings 26, together form the one leg of a U-shaped passage, the other leg 28 of which exhibits at its upper end a weir 29 formed by the upper edge of the wall 17, from which weir the suspension passes to the outlet 21 via the chamber 19. The connection between the two legs of the U-shaped passage is provided by means of openings 30 in the lower part of the wall 24. The lip of the weir 29 is located at such a height that the level of the suspension in the chamber 22 is maintained substantially on a level with or slightly above the lip of the weir 23 of the chamber 18.

The first openings 25 communicate with a constriction (not shown) via the outlet 20. This constriction may comprise a downwardly extending pipe of considerable length and is so adapted in a known manner that when the flow of suspension passing through the inlet 11 is normal, the flow rate of the suspension into the openings 25 is equal to the flow rate of the suspension into the openings 26, and such that variations in pressure head caused by any minor variations in the flow of the suspension incoming through the inlet 11 are insignificant in relation to the pressure drop over the constriction, for example of the order of magnitude of at most 5-10 percent, whereby a constant or at least substantially constant flow is obtained through the openings 25. The conduits associated with the openings 25 discharge at their lower end 31 into the trough-like part 15, to the lower end of which the outlet 20 is connected, while each of the conduits associated with the openings 26 are terminated at their lower ends by a bottom wall 32, which slopes obliquely downwardly towards the wall 24.

If the flow of suspension through the inlet 11 ceases, the flow of suspension across the weirs 23 and 29 will also cease, wherewith the suspension present in the chamber 22 and in the leg 28 of the U-shaped passage will depart through the openings 25. Some suspension will remain, however, in the lower part of the U-shaped passage with the surface of said suspension level with the lowermost point of the upper edges of the partition walls 27. Because of this, solid particles present in the suspension will settle in the lower part of the U-shaped passage. In order to prevent total blockage of the U-shaped passage, the upper edges of the partition walls 27 are inclined downwardly from their opposite ends to form a V-shaped configuration, from locations adjacent the walls 16 and 24, said locations being above the uppermost level 33 of the connection openings 30 between the two legs of the U-shaped passage, to a position 34 which is located at a distance beneath said uppermost level and at a distance from the ends of the partition walls. When suspension again flows through the inlets 11, the sediment will be stirred up and accompany that part of the suspension which flows through the leg 28 and over the weir 29.

In the illustrated embodiment, the wall 24 comprises part of an insert 35 which can be inserted into the vessel 10 between the walls 16 and 17. The wall 24 carries the partition walls 27, which project outwardly from both sides of the openings 30, and also the sloping bottoms 32, the ends of which walls 27 and bottoms 32 remote from the wall 24 being connected by means of a cross wall 36 which, with the insert 35 in position in the vessel 10, abuts the wall 16. For the purpose of localizing the insert in the vessel 10, each of the side walls 13 of the vessel has arranged therein a vertical guide 37 for the end edges of the wall 24, and the lower edge of the wall 24 is arranged to rest against the vessel bottom 14 immediately adjacent the trough-like part 15. Finally, the wall 24 carries on the side thereof facing the wall 17 a box which communicates with the openings 30 and which has a box wall 38 which, for the purpose of optimizing the shape of the leg 28 of the U-shaped passage, slopes obliquely upwardly and outwardly. The upper edge of the box wall 38 abuts the wall 17 and contributes to the correct localization of the insert 35 in the vessel 10.

The invention is not restricted to the aforedescribed and illustrated embodiment, but can be modified within the scope of the following claims.

I claim:

1. A device for taking from a flowing suspension a sample-flow which is of substantially constant flow rate and which is representative of the composition of said suspension, said device being of the kind which comprises a first chamber arranged to receive the flowing suspension and which communicates via a weir with the upper part of a second chamber having first and second openings arranged at the bottom thereof for the removal of the sample-flow and the remaining part of the suspension respectively, said openings being separated from one another by partition walls which extend transversely of said weir over the whole length of the second chamber; and in which the second openings communicate with an outlet via a substantially U-shaped passage and a second weir whose lip is located substantially on the same level as the lip of the weir of the first chamber, while the first openings communicate with a second outlet which is so adapted that with normal flow of the suspension entering the first chamber the flow rate of said suspension into the first openings is substantially equal to the flow rate of said suspension into the second openings, at least one of said partition walls defining communication between the U-shaped passage and said second outlet in a region located lower than the uppermost level of the two legs of the U-shaped passage.

2. A device according to claim 1, characterized in that the upper edge of at least one of said partition walls slopes downwardly from the opposite ends of said partition wall, from locations above the uppermost level of the connection between two legs of the U-shaped passage, to a position located at a distance beneath said uppermost level and at a distance from both ends of the partition wall.

3. A device according to claim 2, wherein said upper edge is of substantially symmetrical V-configuration.

4. A device according to claim 3, wherein said upper edge portions forming said V-configuration enclose an angle of about 50°–135°.

5. A device according to one of claims 1–4, wherein said device comprises a substantially right-angled parallelepipedic vessel, at least one of said weirs being formed by the upper edge of a fixed cross wall extending parallel with and located at a distance from the end walls of the vessel, and said U-shaped passage and said first and second openings being formed in an insert which can be localized in the vessel in a predetermined position adjacent the cross wall, and in that the bottom of the vessel beneath said insert, when said insert is in position in said vessel, has the form of a trough for collecting and conducting away the sample-flow arriving from said first openings.

* * * * *